United States Patent [19]

Kirsch

[11] Plant 4,895

[45] Oct. 12, 1982

[54] LILY NAMED FANCY FREE

[75] Inventor: Ted T. Kirsch, Myrtle Point, Oreg.

[73] Assignee: Sun Valley Bulb Farms, Inc., Myrtle Point, Oreg.

[21] Appl. No.: 215,534

[22] Filed: Dec. 11, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—C. W. Rummler

[57] ABSTRACT

A new and distinct variety of lily plant of the Parkmannis-type oriental hybrid particularly distinguished by the generally flat, outwardly facing, dark reddish-pink and white blossoms which are borne singly on stiff, upwardly extending pedicels carried in raceme arrangement on long, strong stems, and by the dark green, glossy and relatively disease-resistant foliage.

2 Drawing Figures

BACKGROUND OF THE NEW PLANT

This new variety of lily plant originated as a seedling of unknown parentage discovered by me among field grown plants at my nursery in Arcata, Calif. The delicately colored, generally flat, outwardly facing flowers and contrasting dark green foliage of this plant led me to select this plant for propagation and study with the result that I found advantageous and distinctive characteristics in the new plant which give it considerable commercial merit and make it a valuable addition to the field of commercial lily culture for cut flower production. Propagation of this new lily through successive generations by means of scales and tissue culture at Arcata, Calif., has shown that its distinctive characteristics hold true from generation to generation and appear to be firmly fixed.

DESCRIPTION OF THE DRAWING

This new variety of lily plant is illustrated by the accompanying full color photographic drawing which shows a full grown blooming plant in the upper view and a close-up of several blooms in the lower view, the color rendition being as nearly true as can be reasonably obtained by conventional photographic procedures.

DESCRIPTION OF THE NEW PLANT

The following is a detailed description of my new variety of lily plant as observed at Arcata, Calif., in the summer of 1980, the observations having been made of field grown plants and the color designations being according to the R.H.S. Colour Chart published by The Royal Horticultural Society of London, England.

THE PLANT

Origin: Seedling.
Parentage: Unknown.
Classification: Oriental Hybrid-Parkmannis.
Form: A tall single stem from each bulb.
Height: About 3 to 5 feet at maturity.
Growth: Sturdy and upright with excellent strength.
Cane size: The stems grow from a base diameter of about ¼ inch when the plant is at a height of 2 feet, to a base diameter of about ¾ inch when the plant is at a height of about 5 feet.
Foliage:
*Size of leaves at flower cluster.*—Three in number on each pedicel, the one at the base of the pedicel being about 5 inches long and 2¼ inches wide and the one on the pedicel approximately 1 inch from the flower bud being about 4 inches long and 1 inch wide.
*Shape.*—Lanceolate.
*Texture.*—Leathery.
*Aspect.*—Smooth.
*Ribs and veins.*—Distinct, longitudinal veins from base to tip.
Stem bulblet (underground):
*Occurrence.*—One to three on each healthy normal plant at digging time.
*Size.*—From ¼ inch to 1 inch in diameter.
*Color.*—White, with occasional pink shading at the tips.
Bulbs:
*Size.*—From about 6 inches to 10 inches in circumference, depending on age.
*Color.*—White, with yellow and pink overtones. As the bulbs become larger and older, overtones yellow and pink become more and more prominent.

THE BUD

Form: Lanceolate, with acute apex.
Size: Averaging about 3 to 4½ inches long and ¾ inch in diameter.
Number: Usually one on each pedicel, with one to eight buds on the plant stem according to culture and bulb size.
Opening rate: Normal, buds open successively from the lowermost bud to the top bud, which is the last to open.
Color: Reddish-pink and white at the tip of the bud, fading to a darker pink at the base when the sepals are about to divide and the petals begin to unfurl.
Surface texture: Rugose, leathery, with prominent veins.
Pedicel: Strong and generally angled about 75° from the vertical.
*Color.*—Light green on under side and dark maroon on top side, and generally glabrous.
*Length.*—About 2½ to 3 inches.

THE FLOWER

Blooming habit: Annually, blooming profusely in late August.

Size of flower: Medium large, averaging about 6½ to 7 inches in diameter.

Borne: Singly on each pedicel and from larger bulbs, the inflorescence has a raceme arrangement. The size of the bulb and its cultural care will determine the number of blooms and buds to be found on any given inflorescence. From large bulbs, this lily may have three to six blooms open at one time.

Shape: Generally flat, with uniformly spaced petals in star arrangement, with the very tips of the petals curving slightly backward.

Petalage: Normal, three petals and three sepals.

*Form.*—Oval, with obtuse apex, sinuate edges and a center furrow bisecting each petal longitudinally.

*Size.*—Petals are about 4 inches long and about 1⅞ inches wide.

*Color.*—Upon opening, the midrib of the petal is Red Purple RHS 60A and the major portion of the petal is RHS 74D overlaid on a White background color of RHS 155D. The entire petal area except for about 1½ inches of the outer end is profusely covered with Dark Maroon spots.

*Papillae.*—Present on the petals and from 4 to 8 in number.

*Texture.*—Leathery.

*Aspect.*—Velvety.

Fragrance: Sweet.

Discoloration: The color darkens somewhat as the blossom matures.

Effect of weather: The flower generally is not affected by wet weather but will age as temperature rises.

Persistence: The petalage tends to hang on and dry.

Lasting quality:

*On the plant.*—Two or three weeks depending on the size of the bulb and its environmental temperature.

*As a cut flower.*—Ten days to two weeks.

REPRODUCTIVE ORGANS

Stamens:

*Anthers.*—Six in number, about 1 inch long, and in orderly arrangement around the pistil.

*Filaments.*—Length — about 2 inches. Color: greenish-yellow.

Pistils:

Number.—One.

*Style.*—Length — about 3 inches. Color: light green at the base, darkening somewhat at the stigma.

*Stigma.*—Purple gray in color. Ovary: classified as a schizocarp. About 3½ inches long and about 1½ inches in diameter, dehiscing into thirds and containing six rows of seeds of the usual shape for lilies.

I claim:

1. A new and distinct variety of oriental hybrid lily plant substantially as herein shown and described, characterized by its large, generally flat, reddish pink and white, outwardly-facing flowers borne on strong, stiff pedicels, by its dark green and glossy foliage, and by the long lasting quality of the blooms whether on the plant or as cut flowers.

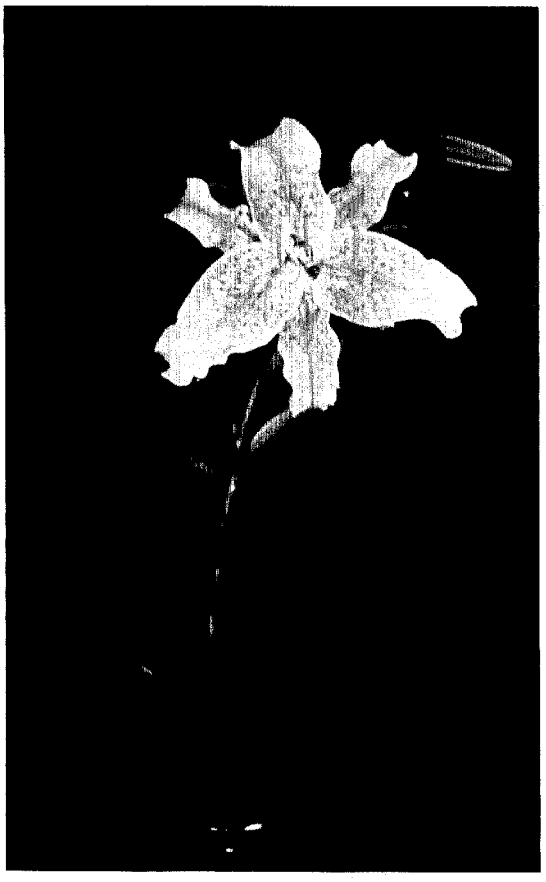
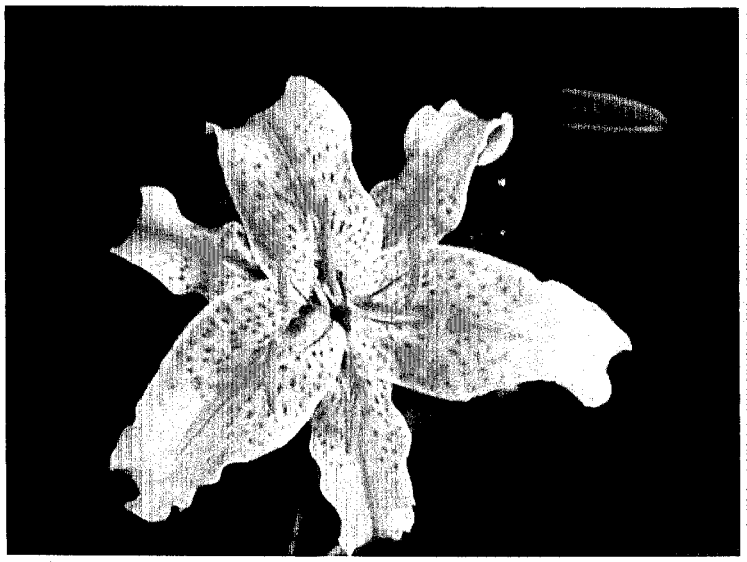

* * * * *